(12) United States Patent
Bunt et al.

(10) Patent No.: US 7,083,590 B1
(45) Date of Patent: Aug. 1, 2006

(54) MULTIPLE MATERIAL DISPENSING

(75) Inventors: Craig Robert Bunt, Hamilton (NZ); Michael John Rathbone, Hamilton (NZ); Shane Burggraaf, Hamilton (NZ); Colin Roger Ogle, Hamilton (NZ)

(73) Assignee: Interag, Hamilton (NZ)

( * ) Notice: Subject to any disclaimer, the term of this patent is extended or adjusted under 35 U.S.C. 154(b) by 313 days.

(21) Appl. No.: 10/048,981

(22) PCT Filed: Aug. 9, 2000

(86) PCT No.: PCT/NZ00/00155

§ 371 (c)(1),
(2), (4) Date: Apr. 9, 2002

(87) PCT Pub. No.: WO01/12101

PCT Pub. Date: Feb. 22, 2001

(30) Foreign Application Priority Data

Aug. 18, 1999 (NZ) .................................... 337318

(51) Int. Cl.
*A61M 1/00* (2006.01)

(52) U.S. Cl. ........................................ 604/30; 604/218

(58) Field of Classification Search ................ 604/143, 604/141, 891.1, 140, 145, 890.1, 20, 21, 604/30, 36, 38, 39, 48, 151, 183, 187, 208, 604/218, 246, 264
See application file for complete search history.

(56) References Cited

U.S. PATENT DOCUMENTS

| | | | |
|---|---|---|---|
| 3,923,058 A | 12/1975 | Weingarten | 128/218 |
| 4,091,807 A | 5/1978 | Dickinson, III | 128/130 |
| 4,323,066 A * | 4/1982 | Bourdon | 128/218 |
| 4,413,391 A | 11/1983 | Renjilian et al. | 28/166 |
| 4,439,184 A | 3/1984 | Wheeler | 604/90 |
| 5,090,963 A | 2/1992 | Gross et al. | 604/132 |
| 5,290,259 A | 3/1994 | Fischer | 604/218 |
| 5,354,264 A * | 10/1994 | Bae et al. | 604/21 |
| 5,460,242 A | 10/1995 | Graf | 184/29 |
| 5,593,552 A * | 1/1997 | Joshi et al. | 204/230.5 |
| 5,599,312 A | 2/1997 | Higashikawa | 604/191 |
| 5,741,275 A | 4/1998 | Wyssmann | 604/143 |
| 5,989,215 A | 11/1999 | Delmotte et al. | 604/82 |
| 6,450,991 B1 * | 9/2002 | Bunt et al. | 604/143 |

FOREIGN PATENT DOCUMENTS

| | | |
|---|---|---|
| EP | 0737484 A2 | 10/1996 |
| NZ | 210601 | 1/1988 |
| NZ | 329338 | 12/1998 |
| WO | WO91/16094 | 10/1991 |
| WO | WO92/07612 | 5/1992 |
| WO | WO94/01165 | 1/1994 |

(Continued)

*Primary Examiner*—Long V. Le
*Assistant Examiner*—Ann Y. Lam
(74) *Attorney, Agent, or Firm*—Jacobson Holman PLLC (57) ABSTRACT

A device suitable for use as an intra vaginal device or as a bolus where, after initiation, a member (usually a plunger) moves with a known movement characteristic and is involved in the stagger release of multiple materials. That moving member is used to time the discharge of one or more material from its reservoir in the device (there being separate powering of the timed discharge) or is used to both time and indirectly power the discharge of one or more material from its reservoir, such discharges preferably being in a staggered manner. Optionally the moving member as a plunger may itself also directly discharge a material from a reservoir.

21 Claims, 11 Drawing Sheets

FOREIGN PATENT DOCUMENTS

| | | |
|---|---|---|
| WO | WO95/13760 | 5/1995 |
| WO | WO96/08280 | 3/1996 |
| WO | WO96/29025 | 9/1996 |
| WO | WO96/37189 | 11/1996 |
| WO | WO97/40776 | 11/1997 |
| WO | WO98/33452 | 8/1998 |
| WO | WO99/07346 | 2/1999 |
| WO | WO99/12593 | 3/1999 |
| WO | WO99/26556 | 6/1999 |
| WO | WO00/37130 | 6/2000 |

* cited by examiner

MULTIPLE MATERIAL DISPENSING

This is a nationalization of PCT/NZ00/00155, filed Aug. 9, 2000, and published in English.

The present invention relates to dispensing apparatus for dispensing an agent or its precursor(s), methods of use thereof and related means, methods and applications.

There are many instances where it is desired to activate or allow the activation of the release of an active agent or its precursor(s) whether as a single dose, a continuous dose or as a pulsile dose. Instances include microprocessor control active delivery of agents as might be used to release a medicament into a body cavity such as, for example, disclosed in PCT/NZ98/00011.

Many forms of such active delivery device (in addition to microprocessor or other logic means capable of empowering the release) utilise a reservoir or barrel having a membrane or piston that separates the formulation of the active agent or its precursor(s) from a gas generating arrangement, eg, a hydrogel and its electrodes.

SUMMARY OF THE INVENTION

The present invention is directed to providing the timing mechanism for dispensing apparatus (preferably which lends itself to an easier manufacturing procedure (as will be described hereinafter in more detail)). It is an object of the present invention to provide such apparatus and related means, methods and procedures.

The present invention has found there can be an effective staggering of materials to be delivered from a device (once initiated by some act) which thereafter is to continue with its delivery regime without a need for further human input where there is reliance on the movement (preferably rectilinearly) of a member or element having a known movement profile or characteristic as the stagger timing mechanism.

In one aspect the invention is a dispensing apparatus capable of expressing material, whether the same or different, from at least two reservoirs, the apparatus being characterised in that actuation means for expressing material from an outlet of a first of said reservoirs (hereafter "primary reservoir") also directly or indirectly expresses or times the expression of material from the outlet(s) of at least one other said reservoir (hereafter "secondary reservoir(s)") but only after a predetermined state of expression of the material from said primary reservoir has occurred.

Preferably said actuation means for expressing material from said primary reservoir includes a piston (hereafter "primary piston").

Preferably said at least one said secondary reservoir at least in part includes a piston capable of expressing its material via its outlet.

In one embodiment said actuation means includes a gas generation unit the gas of which is capable of moving said primary piston.

Preferably said gas generation unit is a resistance circuit actuable to generate gas from the battery providing the powering therefor.

Preferably said gas generation unit includes a hydrogel electrolysed at least in part by a battery powered resistance circuit. In this respect see WO 94/01165, U.S. Pat. No. 5,460,242 and U.S. Pat. No. 5,741,275.

Preferably a switching mechanism is provided to allow the initiation of actuation of said gas generation unit.

In other embodiments said actuation means includes at least one of the group consisting of a spring, an osmotically expanding material, a chemical reaction, compressed gas, evolved or generated gas(es) and a motor.

Preferably said apparatus is capable of being inserted into a body cavity.

Preferably deployable members for retention in a target body cavity are provided.

Preferably said apparatus is of a configuration for a target mammal with retention features for intra vaginal use. See, for example, U.S. Pat. No. 4,091,807, WO 99/07346, WO 95/13760, WO 98/33452 and WO 96/29025.

Preferably at least one of the materials to be expressed is a liquid or liquid formulation.

Preferably at least one of the materials to be expressed is in the form of a solid or a solids formulation.

Preferably at least one of said outlets is sealed, plugged or otherwise closed yet is openable under the forces to act thereon as the associated material is pressed for expression out of such outlet(s).

Preferably at least one of said secondary reservoirs has its material expressible under the action of gas from said gas generation unit bypassing or ducting through said primary piston once the primary piston has moved a predetermined amount.

Preferably (at least) one of said secondary reservoirs has its material expressible under the action of said primary piston coming into contact with and driving a material expressing piston of a said secondary reservoir.

Preferably said primary piston carries a magnet capable of switch actuation for a circuit in turn, once actuated, to cause movement of means to express material from at least one said secondary reservoir.

Preferably said primary piston using a magnet/reed switch interaction can cause an expression of the material from at least one said secondary reservoir.

In another aspect the invention is as previously defined substantially as herein described with reference to any example thereof and/or any of the accompanying drawings.

In another aspect the invention is a dispensing apparatus comprising or including
  an assembly defining partitioned chambers where the partitioning member can be moved by gas pressure increase(s) in one chamber to reduce the volume of the other chamber,
  a battery powered circuit actuable to generate gas within or for said one chamber,
  at least one assembly defining at least one material containing reservoir with an outlet (sealed, plugged or otherwise optionally closed) it or each capable of being reduced in volume by a piston,
  wherein at least one said piston of a said material containing reservoir is moved to express the associated material only once, under the action of said gas generation, said partitioning member has moved a predetermined amount.

Preferably said partitioned chambers have a piston as its partitioning member.

Preferably said one chamber of said partitioned chamber to reduce in volume has an outlet (sealed or otherwise) and contains a material expressible out of said chamber as said volume is reduced.

In another aspect the invention is a dispensing apparatus comprising or including
  an assembly defining partitioned chambers where the partitioning member can be moved to reduce the volume of the other chamber,
  at least one assembly defining at least one material containing reservoir with an outlet (sealed, plugged or otherwise optionally closed) it or each capable of being reduced in volume by a piston, wherein at least one said piston of a said material containing reservoir is moved to express the associated material only once said partitioning member has moved a predetermined amount.

Preferably said partitioning member is movable by mans of at least one of the group consisting of a spring, an osmotically expanding material, a chemical reaction, compressed gas, evolved or generated gas(es) and a motor.

Preferably a said piston of a said material containing reservoir is movable by means of at least one of the group consisting of a spring, an osmotically expanding material, a chemical reaction, compressed gas, evolved or generated gas(es) and a motor.

Preferably said partitioned chambers have a piston as its partitioning member.

Preferably said one chamber of said partitioned chamber to reduce in volume has an outlet (sealed or otherwise) and contains a material expressible out of said chamber as said volume is reduced.

In another aspect the invention is a multiple material dispensing apparatus having a primary reservoir containing a first material expressible via an outlet under the action of a primary piston, and at least one secondary reservoir itself containing a material to be dispensed via an outlet under the action of a secondary piston, wherein said secondary piston is actuable directly by said primary piston after an at least partial expression of the material of the primary reservoir.

In still another aspect the invention is a dispensing apparatus capable of expressing materials, whether the same or different, from at least two reservoirs, the apparatus being characterised in that a piston (hereafter "primary piston") in use will express or cause the expression at least some material from a reservoir and that piston, directly or indirectly, activates or causes the expression of at least some material from at least one other reservoir, the relative timing of the at least partial emptying of the reservoirs between or amongst the reservoirs being predetermined but nonetheless being dependent on said piston and its travel.

In still another aspect the invention is a dispensing apparatus capable of expressing material, whether the same or different, from at least two reservoirs in a delayed manner, the apparatus being characterised in that a member capable in use of moving or being set to move, can, upon predetermined movement occurring to provide the delay or delays, directly or indirectly express or time the expression of material from the outlet(s) of said at least two reservoirs.

Preferably each said reservoir includes a piston.

Preferably said member in use capable of moving, moves under the influence of at least one of the group consisting of a spring, an osmotically expanding material, a chemical reaction, compressed gas, evolved or generated gas(es) and a motor.

Preferably in use said delays are staggered.

Preferably said member capable in use of moving or being set to move is a piston capable of expressing material from its own reservoir.

Preferably said apparatus is in the form of a bolus or intra vaginal device, eg; for use as a bolus.

In another embodiment said apparatus is adapted for release of active ingredients into an environment.

In another aspect the invention consists in a dispensing apparatus capable of expressing materials, whether the same or different, from at least two reservoirs, the apparatus being characterised in that a piston in use that can be initiated to move or which, in its in use site, can move, will express or cause the expression of at least some material from a reservoir and that primary piston also, directly or indirectly, activates or causes the expression of at least some material from at least one other reservoir.

Preferably the expression of at least some material from at least one other reservoir is under the action of a piston in turn moved, initiated to move or allowed to move by the state of movement of the primary piston.

In another aspect the invention consists in a dispensing apparatus capable of expressing materials, whether the same or different, from at least two reservoirs, the apparatus being characterised in that a piston movable under the action of a generated gas in use will express or cause the expression at least some material from a reservoir and that primary piston also, directly or indirectly, activates or causes the expression of at least some material from at least one other reservoir.

In another aspect the invention consists in a device for intraruminal, intra vaginal, or the like body cavity use capable of expressing materials, whether the same or different, from at least two reservoirs, wherein the apparatus is characterised in that a piston in use will express at least some material from a reservoir and that piston directly or indirectly, activates or causes the expression of at least some material from at least one other reservoir.

In another aspect the invention is an intra vaginal device having (i) a progesterone containing material in a primary reservoir, and (ii) oestradiol or an oestradiol containing material in a secondary reservoir, where, in use, a member which moves in a predetermined way provides a delay in the release of (ii) with respect to (i).

Preferably said device has four reservoirs to release in sequence, reliant on said member's movement (a) a progesterone containing material,
(b) oestradiol benzoate,
(c) cloprostenol sodium, and
(d) oestradiol 17β.

Preferably said device is also a device as previously defined.

In one embodiment said device is a bolus for use in a ruminant having in separate reservoirs a trace metal (eg; zinc) and an anthelmintic (eg; ivermectin) which is also a device as previously defined.

In another aspect the invention is, in a plural reservoir (solids and/or liquid) material dispensing apparatus, the use of a directly or indirectly (eg; through gas generation) driven member capable after initiation of progressive movement having predetermined travel characteristics as the initiator and/or force providing member for time staggered expression of material from the reservoirs.

In another aspect the invention is the use of a member initiable to move (directly or indirectly under battery power) in a predetermined progressive manner to act as the timing element in the expression from material from different reservoirs in at least a staggered manner.

Preferably, in acting as the timing element said member applies directly or indirectly force to an expression piston of at least one reservoir.

Preferably said member is itself an expression piston of a material containing reservoir.

In another aspect the invention is a method of, at least in part, serially or sequentially expressing materials from a delivery device, said method comprising actuating a battery powered device to move an element thereof in a substantially known manner to thereby, with delay of such travel, to act, staggered with respect to time, upon a material expression component of each material containing reservoir to thereby express such material via an outlet.

In still another aspect the invention is a method of stagger expressing materials from a delivery device, said method comprising setting, actuating or initiating the device to move an element thereof, firstly, to commence (directly or indirectly) materially expression from a first reservoir of the device, and secondly, after the element has traveled a predetermined distance and as it continues to travel, to commence (directly or indirectly) material expression from another material containing reservoir.

In another aspect the invention is a method of patterning the delivery of plural materials into a body cavity of an animal which comprises or includes the steps of
  introducing into a said cavity a device containing said plural materials,
  discharging at least one of said plural materials from a reservoir under the action of a plunger which reduces the volume of a reservoir available therefor sometime after the initiation of the device, and,
  by (direct or indirect) interaction with said plunger subsequently discharging at least one other material of the device from that material's reservoir within the device.

In one embodiment said device is an intra vaginal device.

In one embodiment said plunger is moved under the action of a gas generation unit.

Preferably said action with said plunger is by abutment with a piston to discharge said at least one other material.

Preferably said interaction with said plunger involves a bypass for a gas but moves said plunger to then in turn act directly upon a piston for discharging said at least one other material.

Preferably said interaction is indirect and involves magnetic switching.

Preferably said device is a bolus or an intra vaginal device and includes means of variable geometry deployable from an insertion condition to a retention condition.

Preferably said method is performed using, as said device, apparatus as previously defined.

In another aspect the present invention consists in a dispensing apparatus capable of expressing materials, whether the same or different, from at least two reservoirs, the apparatus being characterised in that a piston in use will express or cause the expression at least some material from a reservoir and that piston, directly or indirectly, activates or causes the expression of at least some material from at least one other reservoir, the relative timing of the at least partial emptying of the reservoirs between or amongst the reservoirs being predetermined but nonetheless being dependent on said piston and its travel.

Preferably the expressions are linked timewise to the travel of the piston.

Preferably the apparatus is for use as a bolus or as an intra vaginal device. Other uses could be for timed release of actives into any environment, eg; fishtanks, lubricants into bearings, etc.

Preferably the expressions are linked timewise to the travel of the piston.

Preferments in respect of the dispensing apparatus or the bolus of the present invention will now be described.

Preferably said apparatus is of a kind where the piston of said first reservoir advances without rotation. In other forms it may rotate.

Preferably the advancement of the piston of the first reservoir is under the action of a gas and/or an activated electrical circuit.

Preferably the material of at least the first reservoir is a fluid. Preferably that fluid is a liquid. Preferably the liquid is or contains an active ingredient (whether solid or not). In other forms the material may be a gas or a mixture of a gas and liquid. Any such liquids may include a solids content and/or itself is a mixture of multiple liquids. In some instances the material to be expressed from a reservoir can be a solid or almost a solid, eg loose powders, a gel, a capsule, or the like.

In some forms of the present invention at least one and preferably each of the reservoirs is provided with a closed outlet capable of being opened under the direct or indirect action on the contents of the associated reservoir, eg, as would be the case with, for example, a waxed or frangible seal.

Preferably said apparatus has the piston thereof movable under the action of a gas which is generated upon the device being switch activated, eg, at the time of insertion.

In some forms of the present invention the gas may be generated from a hydrogel or the like using an electrolysis dependent gas generation circuit capable of being activated. In still other forms preferably said gas is generated directly from the energisation of a circuit including a gas generation battery.

In some forms of the present invention the first reservoir may in turn discharge its content onto a down stream reservoir, eg utilising as a piston therebetween a seal between the materials for the purpose of discharging first material from the second reservoir.

In still other arrangements there is a direct discharge through a rupturable or dischargeable seal of the material of the first chamber and a sequential movement of the piston towards at least one other reservoir until such time as there is interaction therewith as a result of the pistons movement. Such interaction may be direct contact or penetration. For example, a needle type arrangement could penetrate the piston of the first reservoir to thus allow the action of a gas that moves the first piston directly onto a piston or like member of such a second reservoir. In the same or different apparatus such interaction might mean there might equally be some extension of the piston into the reservoir of another material to itself act as a separate delayed action thereof.

In still other interactions the piston may time (eg by magnetic interaction) some energisation of a release circuit forming part of a release arrangement of another reservoir.

BRIEF DESCRIPTION OF THE DRAWINGS

The invention consists in the foregoing and also envisages constructions of which the following gives examples.

In the accompanying drawings

DETAILED DESCRIPTION OF THE PREFERRED EMBODIMENTS

While the preferred propulsion mechanism for the primary piston is a gas generating or hydrogel cell, other mechanisms may be used.

Other mechanisms that may be employed to drive the primary piston (or secondary pistons, especially following activations by a primary piston via a magnet and reed switch) include;

a spring,
an osmotically expanding material, e.g. gelatin,
chemical reaction, e.g. acid/base reaction resulting in the liberation of CO2,
compressed gas, e.g. a hydrocarbon, and
a motor, e.g. a "watch" or turning screw.

Figure 1:
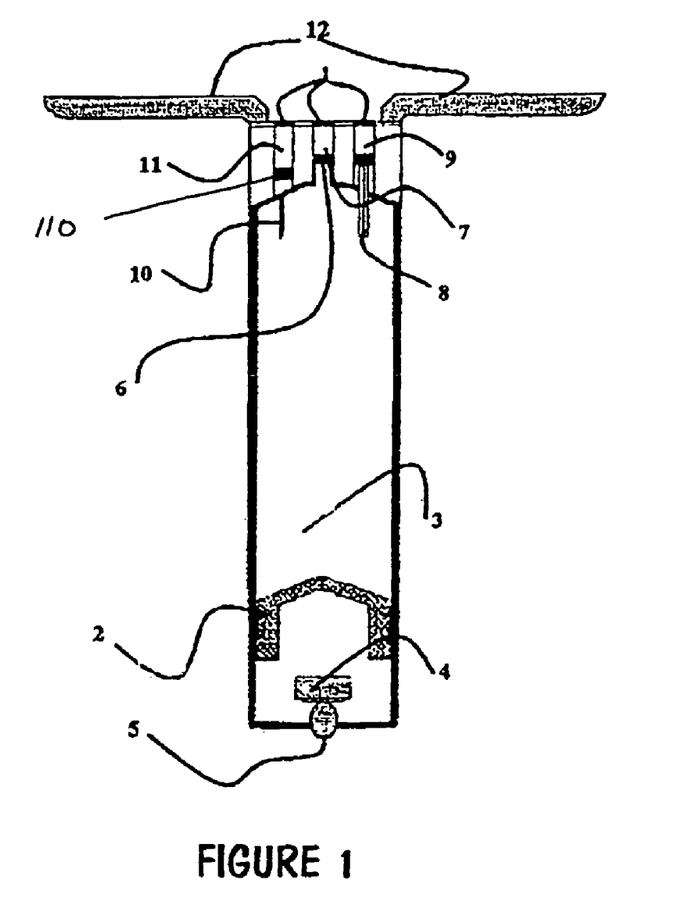
FIG. 1 shows a hybrid apparatus in accordance with the present invention where there can be an actuation of the device and some control of a discharge sequence of materials from different reservoirs in a pre-determined manner.
Figure 2A:
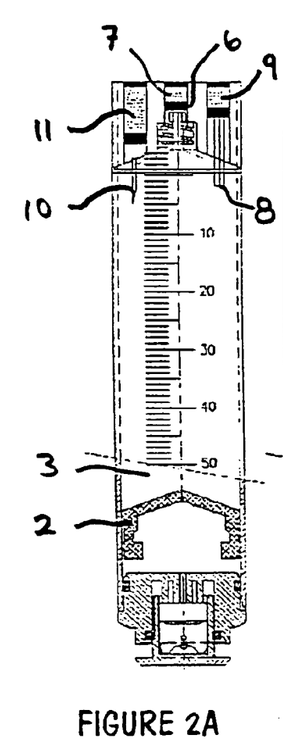
FIGS. 2A to 2D shows a sequence of materials expression using a device substantially similar to that of FIG. 1 with both a piston/needle and piston/piston interaction for the delayed deliveries, FIGS. 3A to 3D in a similar manner to that of FIGS. 2A to 2D shows an expression sequence again with a device similar to that of FIG. 1 but this time with a primary piston interacting directly on a piston of at least two of the secondary reservoirs with stagger timing as to delivery therefrom.
Figure 2B:
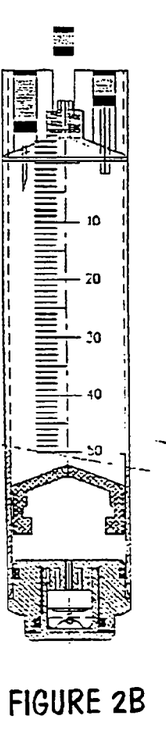
Figure 2C:
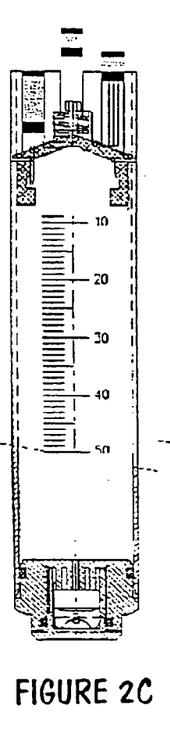
Figure 2D:
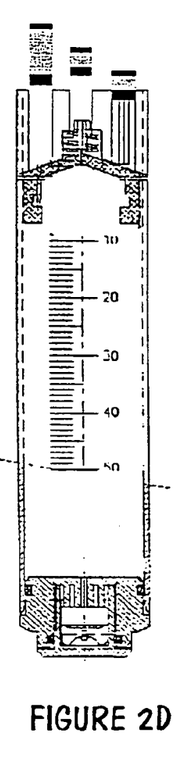
Figure 3A:
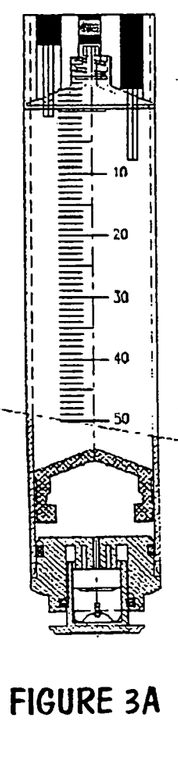
Figure 3B:
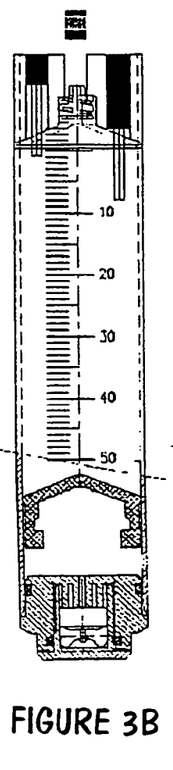
Figure 3C:
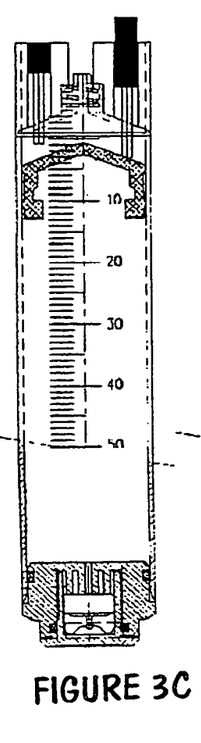
Figure 3D:
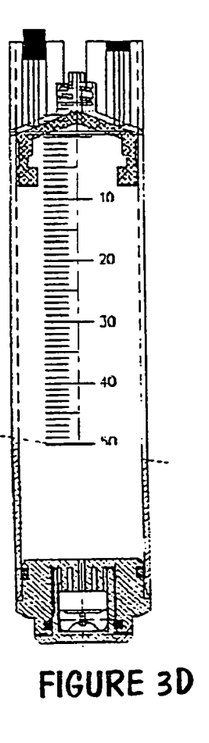

FIG. 1 shows a main barrel or reservoir having an outlet the upper end adjacent to smaller reservoirs. Preferably the formulations are protected within the barrel and smaller reservoirs by rupturible seals 1. A primary piston 2 acts to dispense the material from a primary reservoir 3 as a result of an increase in pressure from a gas cell 4 that is activated by a switch 5. The material of the primary reservoir acts upon a secondary piston 6 of a secondary reservoir 7 to dispense the secondary reservoir material after the rupture of the secondary reservoir seal. The primary piston may also act directly upon a second secondary piston 8 to dispense the contents of a second secondary reservoir 9. The primary piston may also be pierced by a needle 10 thereby enabling gas to by-pass the primary piston and act upon a third secondary piston 110 which in turn dispenses the contents of reservoir 11. Also present on the device are means by way of retention arms 12 for locating the device in a body cavity such as a vagina.

One configuration of the FIG. 1 option is better presented in FIGS. 2A to 2D. As the primary piston commences its migration towards the secondary reservoir, a dosage material (e.g. tablet) located within the secondary reservoir is expelled. Towards the end of the primary pistons migration it acts upon a second secondary piston whilst simultaneously being pierced by a needle. This action has two results;

(1) a dosage material in the second secondary reservoir is expelled, and
(2) hydrogen from the gas cell is able to bypass the primary piston in order to act upon the third secondary piston of the third secondary reservoir and, once sufficient pressure has been reached, expel the contents of said third secondary reservoir.

A different configuration is presented in FIGS. 3A to 3D. As the primary piston commences its migration towards the secondary reservoir a dosage material (e.g. tablet) located within the secondary reservoir is expelled. Towards the end of the primary pistons migration it acts upon a second secondary piston and thereby a dosage material in the second secondary reservoir is expelled. Following this action the primary piston commences action upon a third secondary piston and thereby a dosage material in the third secondary reservoir is expelled.

Figure 4:
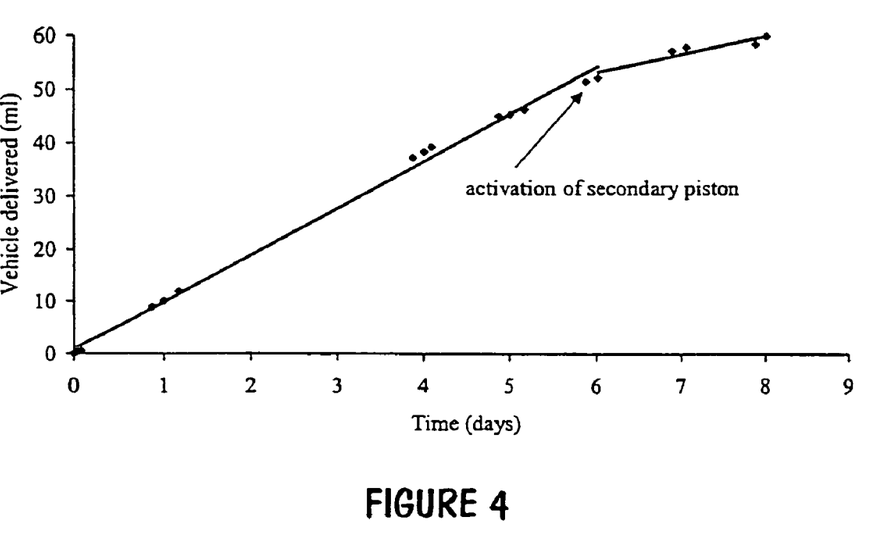
FIG. 4 shows the rate of vehicle delivery for a device of a kind as shown in FIG. 1 in a simplified form.

FIG. 4 shows the rate of vehicle delivery from a device similar to that represented in FIG. 1 with the exception that the needle 10 and piston 11 are absent.

Figure 5:
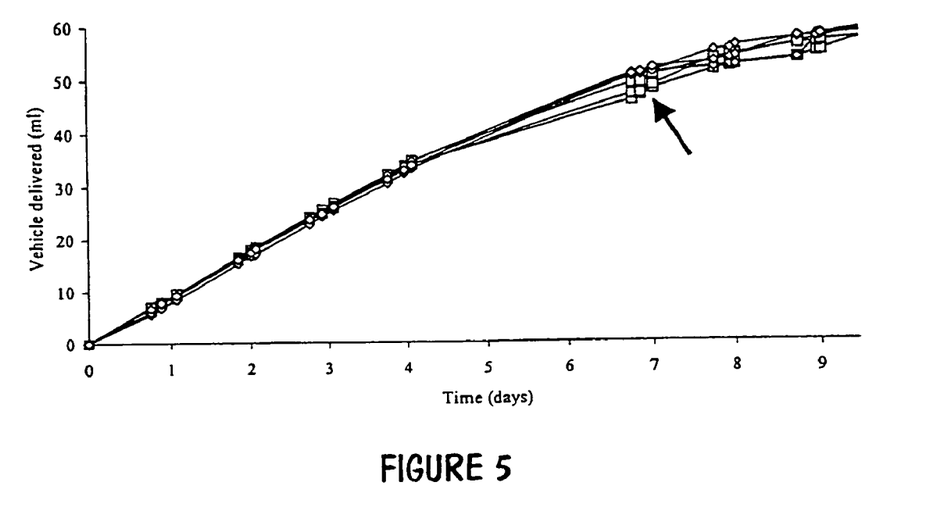
FIG. 5 shows the effect of the needle and piston (diamond) or piston only (square) on delivery rate at 38° C. of vehicle from an infusion reservoir of a device possessing the bolus reservoir option as depicted in the embodiments shown in FIGS. 2A to 2D.

The action of the primary piston coming into contact with a secondary piston reduces the flow of vehicle from the infusion reservoir (FIG. 5). However no additional reduction in flow of vehicle from the primary reservoir is observed as a result of the action of the primary piston coming into contact with the needle as present in said third secondary reservoir mechanism of FIGS. 2A to 2D (see FIG. 5).

In FIG. 5 the arrow represents the time point at which the primary piston comes into contact with the second secondary piston and/or needle. The vehicle was aqueous 2% HPMC held at 38° C. The interaction between the needle and piston as shown by the diamonds and the interaction between the piston with a piston is shown with the squares.

Figure 6:
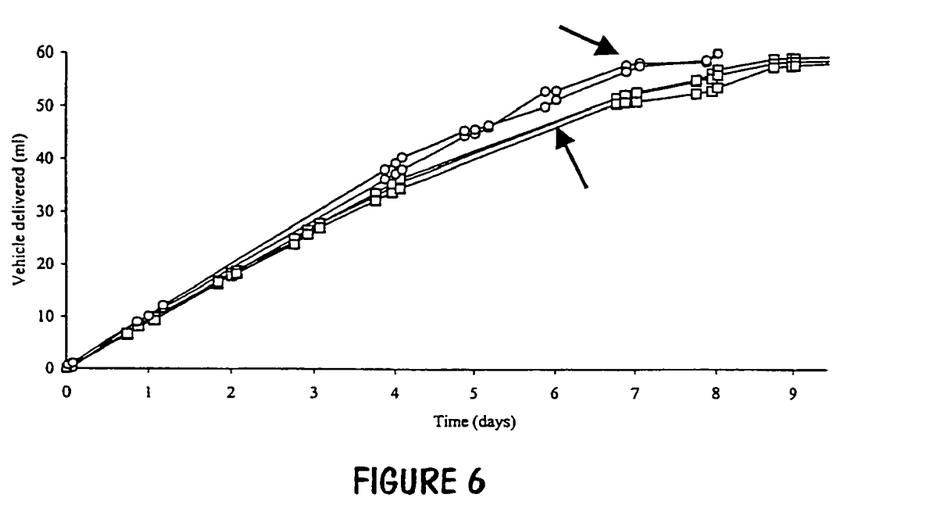
FIG. 6 shows the effect of short secondary piston (circle) or long secondary piston (square) upon flow rate at 38° C. of vehicle from the infusion reservoir of a device possessing piston/piston interaction options as shown in options of FIGS. 2A to 2D and more particularly 3A to 3D.

The action of the primary piston coming into contact with a second secondary piston reduces the flow of vehicle from the primary reservoir (FIG. 6). However selection of long (i.e. projecting further into the primary reservoir) or short pistons for the second secondary reservoir piston and altering the external resistor allows for control of the flow rate from the primary reservoir (FIG. 6).

In FIG. 6 the vehicle is aqueous 4% HPMC at 38° C. and the circles depict the effect of a short piston whilst the square depict the effect of a long piston. The piston options are those depicted as piston to piston interactions in FIGS. 2A to 2D and 3A to 3D.

Figure 7:
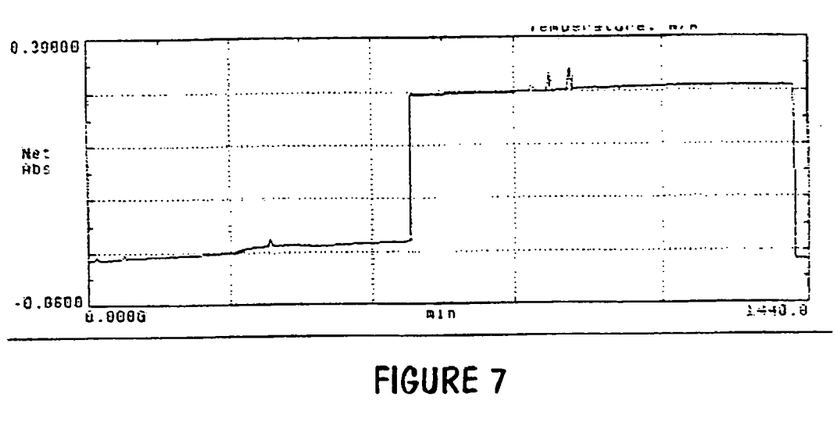
FIG. 7 shows a plot to show the effect of the static resistance of the piston and seals of a primary bolus reservoir and the subsequent influence thereof on time lag between initiation of hydrogen production of a gas cell and release of a secondary reservoir material and vehicle from the primary reservoir, FIG. 7 showing the release of fluorescence from a secondary reservoir with a high static pressure piston.
Figure 8:
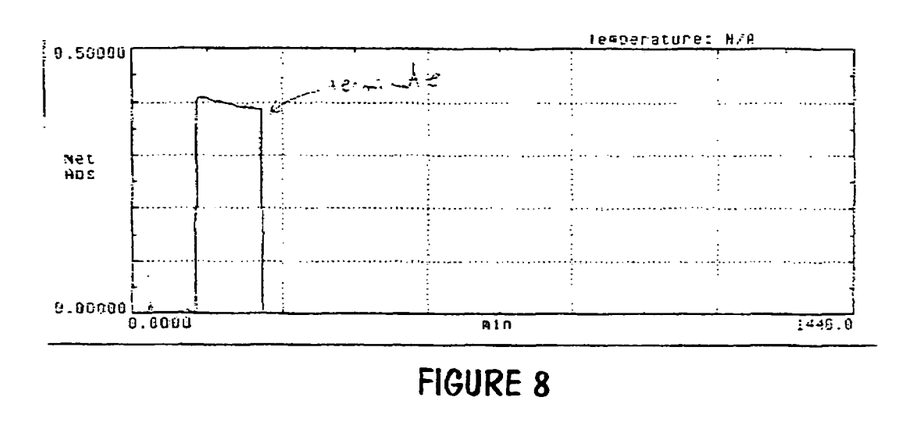
FIG. 8 is a similar plot to that of FIG. 7 but in respect of a low static pressure piston.

The static resistance of the piston and seals of the secondary reservoir influences the time lag between initiation of hydrogen production by the gas cell and release of the secondary reservoir dosage material and vehicle from the primary reservoir (see FIGS. 7 and 8 and Table 1).

Table 1. Effect of high static pressure (2 points of contact between piston and reservoir walls) and low static pressure (1 point of contact between piston and reservoir walls) upon the lag between initiating hydrogen production by the gas cell and release of a dosage unit from the secondary reservoir.

| Replicate | High friction | Low friction |
|---|---|---|
| 1 | 655–660 mins | 125 mins |
| 2 | Did not release | 410 mins |

Choice of appropriate rod lengths for the second secondary delivery mechanism and static pressure of the pistons within each individual reservoir would enable the selection of any desired delivery rate and profile.

FIG. 7 shows the release of fluorescence from the secondary reservoir with a high static pressure piston whilst FIG. 8 shows the release of fluorescence from the secondary reservoir with a low static pressure piston.

Figure 9:
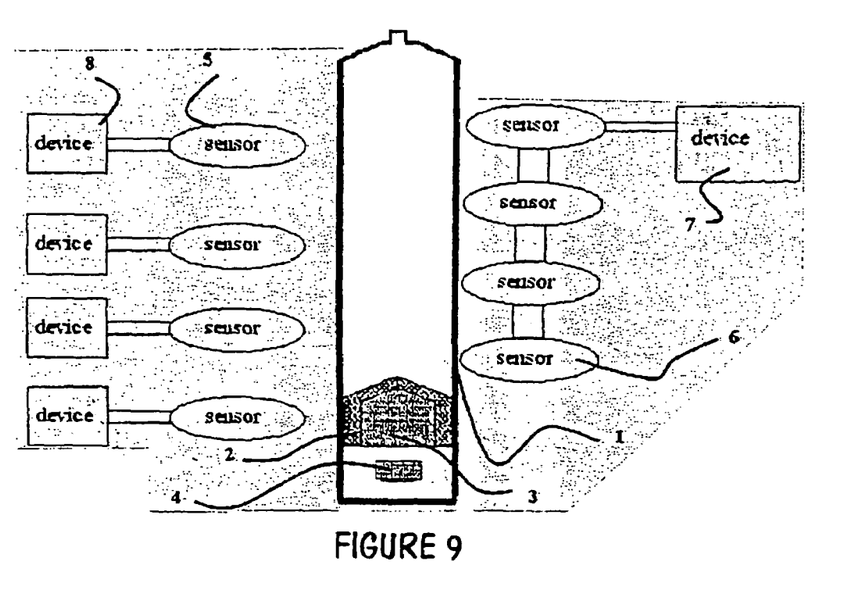
FIG. 9 shows the use of an interaction with the piston to time subsequent discharges.
Figure 10A:
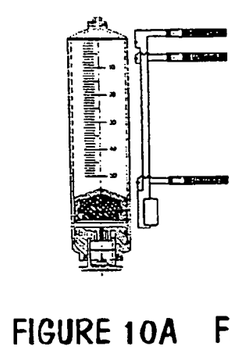
FIGS. 10A through 10D show a device having (shown diagrammatically and not in an assembly) a sequence of three secondary reservoirs capable of being activated by passage past, for example, a read switch of a magnet that moves as the moveable element or member.
Figure 10B:
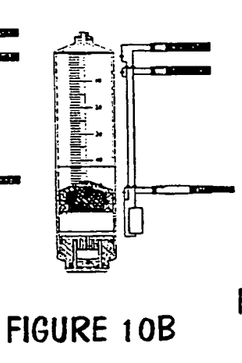
Figure 10C:
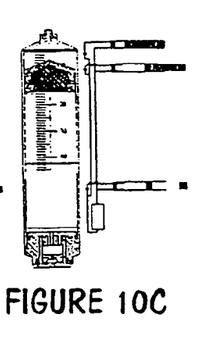
Figure 10D:
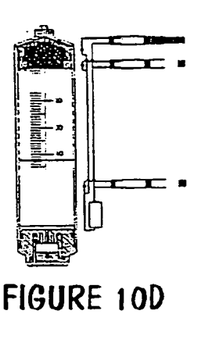

FIG. 9 shows a main barrel or reservoir 1 in which a piston 2 containing a magnetic material 3 is enabled to migrate within the main barrel as a result of an increase in pressure from a gas cell 4. The magnet material is able to activate individual sensors 5 or sensor part or an array 6 which in turn control the action of a device(s) 7 and/or 8.

In Vivo Performance of Multiple Material Dispensing Option of FIGS. 3A to 3D

An in vivo trial investigated the performance of the bolus reservoir mechanism of FIGS. 3A to 3D. Devices were assembled as per FIGS. 3A to 3D, and inserted into the vagina of normal cattle for 9 days. It was visually confirmed upon removal of the devices that all chambers were activated and the dosage units therein delivered.

Description of Multiple Material Dispensing Option of FIGS. 10A to 10D

The configuration of this option is presented in FIGS. 10A to 10D. As the primary piston commences its migration towards the second reservoir dosage material (e.g. tablet) located within said secondary reservoir are expelled due to the action of a magnet within the primary piston activating sequential reed switches thereby initiating the electrolytic production of gasses.

In Vitro Performance of Multiple Material Dispensing Option of FIGS. 10A to 10D

Three devices as per FIGS. 10A to 10D and FIG. 9 were constructed. Activation and expulsion of dosage units from all bolus reservoirs was visually confirmed.

In Vivo Performance of Multiple Material Dispensing Option of FIGS. 10A to 10D

An in vivo trial investigated the performance of bolus reservoir mechanism of FIGS. 10A to 10D. Devices were inserted into the vagina of normal cattle for 9 days. It was visually confirmed upon removal of the devices that all chambers had been activated and the dosage units therein delivered.

Preferred Multiple Material Dispensing Option

Figure 11:
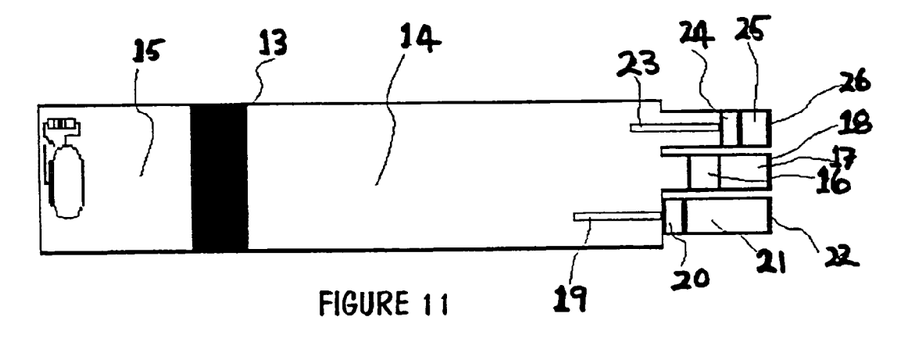
FIG. 11 shows a most preferred form of the present invention having materials discharged from the primary reservoir under the action of a primary piston (moved by gas being generated after initiation), the primary piston subsequently, by abutment on piston extensions of two secondary reservoirs, leading to the staggered discharge from the secondary reservoirs.

A preferred configuration is detailed in FIG. 11 and Table 2. It consists of a cylinder that is divided by a primary piston 13 in a primary reservoir 14, containing the formulation, and part 15, containing the gas and the gas producing components. The action of primary piston 13 upon the formulation contained in the primary reservoir 14 causes the secondary piston 16 to expel the material of the secondary reservoir 17 following the rupture of the secondary reservoir seal 18.

Following the expulsion of formulation primary piston 13 migrates towards the outlet of secondary reservoir 17 thereby coming into contact with rod 19. Rod 19 of the second secondary piston 20 acting under the influence of the primary piston 13 drives the second secondary piston 20 to expel the material of the second secondary reservoir 21 following the rupture of the second secondary seal 22.

Following further expulsion of formulation the primary piston 13 migrates further towards the outlet of the third secondary reservoir 17 thereby coming into contact with rod 23 of the third secondary piston 24. Rod 23 acting under the influence of the primary piston 13 drives the third secondary piston 24 to expel the contents of the third secondary reservoir 25 following the rupture of the third secondary reservoir seal 26.

TABLE 2

Physical parameters of design brief for electronically modulated intravaginal synchrony device.

| Parameter | Specification |
|---|---|
| Gross physical dimensions | |
| Delivery component outer diameter (cm) | 2.5 |
| Delivery component length (cm) | 13 |
| retention mechanism width (cm) | 15 |
| Primary reservoir (1) | |
| Volume (ml) | 30 |
| Delivery rate (ml/day) | 3.33 |
| Secondary reservoir (5) | |
| rod protrusion into primary reservoir (%) | NA |
| Volume (ml) | 0.10 |
| Second Secondary reservoir (8) | |
| rod protrusion into primary reservoir (%) | 11 |
| Volume (ml) | 0.10 |
| Third secondary reservoir (11) | |
| rod protrusion into primary reservoir (%) | 1 |
| Volume (ml) | 0.10 |

EXAMPLE 1

Reservoir Contents for Intra Vaginal Product

Primary reservoir material:
  15 mg/ml progesterone dissolved in ethanol thickened with 4% hydroypropyl methyl cellulose (P4)

Secondary reservoir material:
  a tablet, liquid or semi-solid dosage unit of 10 mg oestradiol benzoate (ODB)

Second secondary reservoir material:
  a tablet, liquid or semi-solid dosage unit of 1000 mcg of cloprostenol sodium (PG)

Third secondary reservoir material:
  a tablet, liquid or semi-solid dosage unit of 7.2 mg oestradiol 17beta (E17b)

EXAMPLE 2

Contents of Intraruminal Product

Primary reservoir contents—Zinc oxide liquid or semi-solid formulation

Secondary reservoir(s)—tablet, liquid or semi-solid Ivermectin 60 mg

The invention claimed is:

1. Dispensing apparatus for retention in a body cavity of a target mammal and for dispensing multiple materials in the body cavity, said dispensing apparatus comprising
   a housing,
   a primary reservoir with a primary outlet from the housing,
   a secondary reservoir with a secondary outlet from the housing,
   a primary piston,
   a secondary piston,
   said primary piston being directly contactable with said secondary piston and said primary piston expressing a material in said primary reservoir out of said primary outlet,
   said secondary piston expressing a material in the secondary reservoir out of said secondary outlet,
   a force generator to act on said primary piston and actuable to cause movement of the primary piston to cause expression of the material in said primary reservoir from the primary outlet,
   said movement of said primary piston causing partial expression of the material of the primary reservoir prior to said direct engagement with said secondary piston, and
   engagement of said primary piston with said secondary piston causing movement of said secondary piston to cause co-expression of the material in the primary reservoir and the secondary reservoir from the primary outlet and the secondary outlet, respectively.

2. Dispensing apparatus as claimed in claim 1 wherein said force generator is a gas generation unit capable of generating gas which applies pressure to and moves the primary piston.

3. Dispensing apparatus as claimed in claim 2 wherein said gas generation unit is or includes a resistance circuit actuable to generate gas from a battery providing power in the resistance circuit.

4. Dispensing apparatus as claimed in claim 2 wherein a switching mechanism is provided for powering up the gas generation unit.

5. Dispensing apparatus as claimed in claim 1 wherein said gas generation unit includes a hydrogel electrolysed at least in part by a battery powered resistance circuit.

6. Dispensing apparatus of claim 1 further comprising an intravaginal device and the primary material is or includes progesterone.

7. Dispensing apparatus of claim 6 wherein, upon activation of the force generator, progesterone is infused over a period of days into the recipient mammal with expression into the vaginal tract at times during such infusion of at least one of
   (i) an oestradiol, and
   (ii) a prostaglandin.

8. Dispensing apparatus as claimed in claim 1, wherein said primary reservoir outlet is sealed prior to being opened under action of the primary material as the primary material is pressurised by the primary piston.

9. Dispensing apparatus as claimed in claim 1 wherein said secondary reservoir outlet is sealed prior to being opened under action of the secondary material as the secondary material is pressurised or moved by the secondary piston.

10. Dispensing apparatus capable of retention in a body cavity of a target mammal and for dispensing multiple materials, said dispensing apparatus comprising
    an assembly defining, in part, a primary reservoir, a secondary reservoir with an outlet and a second secondary reservoir with an outlet,
    a primary piston disposed in said assembly and movable to vary the volume of said primary reservoir,
    a second secondary piston for the second secondary reservoir disposed in said assembly and movable to reduce the volume of the second secondary reservoir,
    a force generator to act on said primary piston and actuable to cause, in use, after body cavity insertion and in the absence of an external force, a predetermined progressive reduction of the volume of said primary chamber by the primary piston over a period of time,
    a liquid or liquid formulation primary material in said primary reservoir expressible via said secondary reservoir outlet under the action of the primary piston, and
    a secondary compound, composition or formulation material in the secondary reservoir expressible out of the secondary reservoir outlet under direct or indirect action of the primary piston,
    a compound, composition or formulation second secondary material in the second secondary reservoir expressible out of the second secondary reservoir outlet under the action of the second secondary piston,
    wherein, in use, without mixing of the materials prior to each egressing from its outlet, said primary piston after sufficient movement causes expression of the secondary material and thereafter a partial expression of the primary material from the primary reservoir, and
    wherein said primary piston continues to move and reduce the volume of the primary reservoir whilst both
    (2) continuing to express the primary material, and
    (3) bearing on the second secondary piston so as to cause the second secondary material to be expressed from the second secondary reservoir outlet under the action of the second secondary piston as that the second secondary piston reduces the volume of the second secondary reservoir.

11. Dispensing apparatus of claim 10, wherein at least one of the secondary reservoir and second secondary reservoir outlets are sealed prior to being opened under either direct or indirect action of the primary piston.

12. Dispensing apparatus of claim 10, wherein said force generator is a gas generation unit capable of generating gas which applies pressure to and moves the primary piston.

13. Dispensing apparatus as claimed in claim 12, wherein a switching mechanism is provided for powering up the gas generation unit.

14. Dispensing apparatus of claim 10, wherein said force generator acts on the primary piston to cause pressurisation of the primary material, and after sufficient time, to cause rupture of a secondary reservoir seal thus causing expression of said secondary material, and
    wherein said primary piston continues to move and reduce the volume of the primary reservoir causing expression of said primary material via said secondary reservoir outlet.

15. Dispensing apparatus of claim 10, wherein said secondary reservoir contains a secondary piston, and
    wherein said secondary piston is disposed in said secondary reservoir, and
    wherein movement of the primary piston under action of the force generator causes the secondary piston to expel into the body cavity thus expressing the secondary material from the secondary reservoir, and wherein said primary piston continues to move and reduce the volume of the primary reservoir causing expression of said primary material via said secondary reservoir outlet.

16. Dispensing apparatus of claim 10, comprising a plurality of second secondary reservoirs, each with an outlet, each with a second secondary piston and each with a second secondary material.

17. Dispensing apparatus as claimed in claim 16, wherein in each of at least two second secondary reservoirs, there is a different second secondary material.

18. Dispensing apparatus as claimed in claim 17, wherein each of two second secondary reservoirs is adapted to express its second secondary material during expression of the primary material.

19. Dispensing apparatus capable of retention in a body cavity of a target mammal and for dispensing multiple materials, said dispensing apparatus comprising an assembly defining, in part, a primary reservoir with an outlet and, in part, a secondary reservoir with an outlet, a primary piston disposed in said assembly and movable to vary the volume of said primary reservoir, a secondary piston for the secondary reservoir disposed in said assembly and movable to reduce the volume of the secondary reservoir, a force generator to act on said primary piston and actuable to cause, in use, after body cavity insertion and in the absence of an external force a predetermined progressive reduction of the volume of said primary reservoir by the primary piston over a period of time, a liquid or liquid formulation primary material in said primary reservoir expressible out of the primary reservoir outlet under the action of the primary piston, a compound, composition or formulation secondary material in the secondary reservoir expressible out of the secondary reservoir under the action of the secondary piston, wherein, in use, without mixing of the materials prior to each egressing from its outlet, said primary piston after sufficient movement to provide a partial expression of the primary material from the primary reservoir, continues to move and reduce the volume of the primary reservoir whilst both (4) continuing to express the primary material, and (5) bearing on the secondary piston so as to cause secondary material expression from the secondary reservoir outlet under the action of the secondary piston as the secondary piston reduces the volume of the secondary reservoir, and a plurality of secondary reservoirs, each with an outlet, each with a secondary piston and each with a secondary material.

20. Dispensing apparatus as claimed in claim 19, wherein in each of at least two secondary reservoirs, there is a different secondary material.

21. Dispensing apparatus as claimed in claim 20, wherein each of two secondary reservoirs is adapted to express its secondary material during expression of the primary material.

* * * * *